United States Patent [19]

Wiesen et al.

[11] Patent Number: 4,873,338

[45] Date of Patent: Oct. 10, 1989

[54] PROCESS FOR THE PREPARATION OF 2-AMINO-5-ACYLAMINO PHENOLS AND STARTING COMPOUNDS SUITABLE THEREFOR

[75] Inventors: Heinz Wiesen, Euskirchen; Erich Wolff, Solingen, both of Fed. Rep. of Germany

[73] Assignee: Agfa-Gevaert Aktiengesellschaft, Leverkusen, Fed. Rep. of Germany

[21] Appl. No.: 123,920

[22] Filed: Nov. 23, 1987

[30] Foreign Application Priority Data

Dec. 6, 1986 [DE] Fed. Rep. of Germany ....... 3641825

[51] Int. Cl.$^4$ ................ C07D 213/64; C07C 102/00; C07C 143/675; C07C 103/30
[52] U.S. Cl. .................................... 546/293; 562/48; 562/52; 546/294; 546/300; 548/169; 548/170; 548/171; 548/172; 548/204; 548/205; 548/235; 548/236; 548/251; 548/476; 548/513; 548/545; 548/549; 549/65; 549/479; 564/50; 564/79; 564/92; 564/99; 564/162; 564/170; 564/175; 564/184; 564/218
[58] Field of Search ................. 564/162, 175, 184, 50, 564/79, 92, 99, 218, 170; 548/476, 513, 169, 170, 171, 172, 204, 205, 235, 236, 251, 545, 549; 260/509; 546/293, 294, 300; 549/65, 479

[56] References Cited

U.S. PATENT DOCUMENTS 2,556,664  6/1951  Smith et al. .......................... 548/476
3,892,802  7/1975  Podesva et al. ..................... 548/476
4,025,505  5/1977  Gschwend et al. ................. 548/476

Primary Examiner—Mary E. Ceperley
Attorney, Agent, or Firm—Connolly and Hutz

[57] ABSTRACT

Compounds corresponding to Formula I

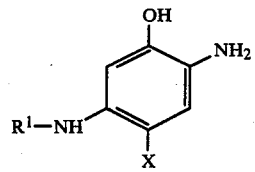

wherein
$R^1$ denotes an acyl group and
X denotes hydrogen, halogen, alkoxy, aroxy, $SO_3H$ or a heterocyclic group attached through —O— or —N<
are prepared form a compound corresponding to Formula II

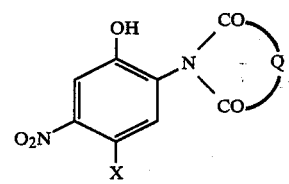

wherein
X has the meaning already indicated and Q denotes the group required for completing a dicarbonimide ring
by reduction of the said compound to the amino compound and acylation into a compound corresponding to Formula III

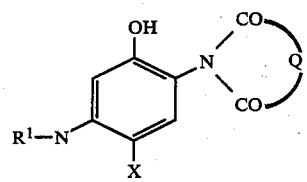

wherein
X, Q and $R^1$ have the meanings indicated
followed by conversion of the compound corresponding to Formula III into a compound corresponding to Formula I by hydrazinolytic or hydrolytic decomposition of the dicarbonimide ring.

3 Claims, No Drawings

PROCESS FOR THE PREPARATION OF 2-AMINO-5-ACYLAMINO PHENOLS AND STARTING COMPOUNDS SUITABLE THEREFOR

This invention relates to a process for the preparation of 2-amino-5-acylamino phenols.

2-amino-5-acylamino phenols are suitable intermediate compounds for the preparation of phenolic cyan couplers such as those described as cyan couplers for colour photographic recording materials in, for example, US-A-2 369 929, US-A-2 772 162, US-A-2 895 826, US-A-3 880 661, US-A-0 028 099, EP-A-0 067 689, EP-A-0 175 573, and EP-A-0 184 057. Cyan couplers of this kind contain an acylamino group both in the 2-position and in the 5-position. If such couplers are to be suitable for use in colour photography, the 4-position (para to the phenolic hydroxyl group) must either be unsubstituted or carry a substituent which is split off in the process of chromogenic development so that a cyan indoaniline dye can be produced by the coupling reaction with the oxidation product of a colour developer. The properties of the cyan couplers may be varied by varying the two acylamino groups, the colour characteristics depending to a greater extent on the structure of the acylamino group in the 2-position while the emulsification properties, diffusion properties (resistance to diffusion) and stability depend mainly on the structure of the acylamino group in the 5-position, which may contain a ballast residue.

In one known method of preparation, 2-nitro-5-aminophenols may be used as starting materials. In this method, the 5-amino group is first acylated and the nitro group in the 2position is then converted into an amino group by reduction and the resulting compound then is further reacted in a suitable manner to form the desired coupler. This method has the advantage that one common preliminary compound may be used for the preparation of different couplers having the same 5-acylamino group and the choice of acylamino group in the 2-position which determines the colour characteristics of the coupler may be postponed to a comparatively late stage of the whole process. The disadvantage, however, is that 2-nitro-5-aminophenol required as starting compound is not readily available.

In another known method of prpeparation, 2-amino-5-nitrophenols may be used as starting materials, which are first acylated in the 2-amino position to introduce the necessary group to determine the properties of the coupler. The 5-nitro group is subsequently reduced and the resulting amino group is acylated. The starting compound used for this method is comparatively readily available but the decision as to the structure of the coupler to be produced must be made at an early stage and if several different couplers having the same 5-acylamino group are to be prepared from the same starting compound, then the same sequence of steps must be carried out for each coupler, starting from the original acylation product. This is due to the fact that the sequence in which the two acylamino groups are formed is determined by the structure of the starting compound. Moreover, this method of synthesis is unsuitable for various cyan couplers as problems of solubility and oxidation occur at the stage of reduction, which may prevent synthesis or at least render it difficult. This applies particularly to the preparation of some couplers of the 2-phenylureido-5-acylaminophenol series.

In order that an acylamino group, optionally containing a ballast residue, may first be obtained in the 5-position when 2-amino-5-nitrophenol is used as starting material, it would be necessary first to protect the 2-amino group by temporarily blocking it with a suitable protective group and this protected amino group would subsequently have to be released by suitable methods after the amino group obtained from the 5-nitro group has been acylated. No suitable protective groups have hitherto been available for this purpose.

The following methods, for example, are known:

1. Hydrazinolysis of 2-mercapto-5-nitrobenzothiazole (Bower & Stephens, J. Chem. Soc. 1951, 325) to the 5-nitro-2-aminophenol. Hydrazinolytic decomposition of 5-acylamino-2-mercaptobenzothiozoles cannot be carried to completion and is accompanied by the formation of by-products.

2. Blocking of the amino group in 5-nitro-2-aminophenols by acylation with alkyl or aryl carboxylic acids to form 2-alkyl (-aryl)-5-nitrobenzoxazoles (DE-A-35 21 454). Hydrolytic opening of the benzoxazole ring is possible after reduction of the nitro group and attachment of a ballast residue but deacylation cannot be carried out without at the same time splitting off the ballast residue.

3. Formylation of amines, e.g. with formic acid. 5-nitro-2-aminophenol can be converted quantitatively into 5-nitro-2-formamidophenol. Reduction of the nitro group followed by introduction of a ballast residue and deacylation to the 5-acylamino-2-aminophenol proceed readily but the intermediate stage, namely the 5-acylamino-2-formamidophenol carrying the ballast residue is not crystallizable so that the purification necessary at this stage cannot be carried out and the method is therefore unusable.

4. Protection of the amino group in 5-nitro-2-aminophenol with perfluorbutyric acid. 5-acylamino-2-aminophenols carrying a ballast residue and protected only by perfluorbutyric acid can be prepared on a relatively large scale and converted hydrazinolytically into 5-acylamino-2-aminophenols which can be isolated by crystallization. This process, however, is uneconomical since perfluorbutyric acid is not only expensive but is lost after hydrazinolytic decomposition.

5. Conversion of o-aminophenols to benzoxazolones by reaction with phosgene. 5-nitrobenzoxazolones prepared from 5-nitro-2-aminophenol can be converted into 5-acylaminobenzoxazolones. Hydrolytic opening of the oxazolone ring without the 5-acylamino group being attacked succeeds only partially. Chromatographic working up of the product was found to be necessary in all cases.

6. Formation of carbamates from 5-nitro-2-aminophenols. N-(5-nitro-2-aminophenyl)-carbamic acid ester can readily be prepared by means of chloroformic acid esters. After reduction of the nitro group and introduction of a ballast residue, the protective group can be split off by hydrolysis but the resulting o-aminophenols are always obtained in a dark coloured, resinous form which will not crystallize.

It is an object of the present invention to provide an improved method for the preparation of 2-amino-5-acylamino phenols.

A process has now been found for the preparation of compounds corresponding to Formula I

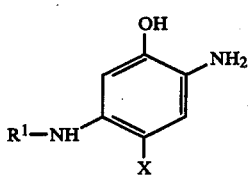

wherein

R¹ denotes an acyl group and

X denotes hydrogen, halogen, alkoxy, aroxy, SO₃H or a heterocyclic group attached through —O— or —N<, which process is characterised in that a compound corresponding to Formula II

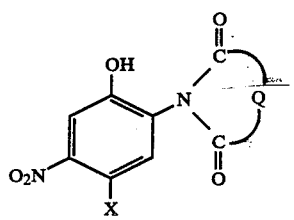

wherein

X has the meaning indicated and Q denotes the group required for completing a dicarbonimide ring is converted by reduction to the amino compound and acylation into a compound corresponding to Formula III

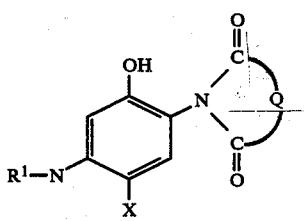

wherein

X, Q and R¹ have the meanings indicated and in that the compound corresponding to Formula III is converted into a compound corresponding to Formula I by hydrazinolytic or hydrolytic decomposition of the dicarbonimide ring.

An acyl group denoted by R¹ in Formula I or Formula III is derived from an aliphatic or aromatic carboxylic or sulphonic acid or from a carbamic or sulphamic acid. Examples of such acyl groups include groups of the Formula

R²—CO— wherein

R² preferably denotes an optionally substituted alkyl or aryl group. A substituted alkyl group denoted by R² may have, for example, the following structure:

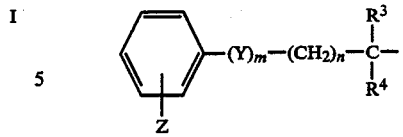

wherein

R³ and R⁴ denote, independently of one another, H or alkyl,

Y denotes —O— or —S—,

Z denotes one or more substituents, e.g. halogen, alkyl, alkoxy, alkylthio, alkylsulphonyl, acylamino, sulphonamido or sulphamoyl, m represents 0 or 1 and, n represents 0 or an interger from 1 to 3.

The acyl group denoted by R¹ frequently functions as a ballast residue. The alkyl groups contained in this acyl group may therefore contain, for example, 1 to 20 carbon atoms and they may be branched. The following are examples of such alkyl groups: methyl, ethyl, propyl, isopropyl, butyl, isobutyl, t-butyl, t-amyl, hexyl, decyl, dodecyl, octadecyl.

When X in Formula I, II or III is halogen, it may, for example, stand for fluorine, chlorine, or bromine. When X stands for an alkoxy group, an aroxy group or a heterocyclic group attached through —O— (for example, furyl, pyridyl, thienyl, tetrazolyl, oxazolyl, thiazolyl), these groups may in turn be substituted, e.g. with alkoxy, aroxy, amino, acylamino, alkylthio, alkylsulphonyl or arylsulphonyl. A heterocyclic group attached through —N< may be, for example, a cyclic imide group derived from the imide of a phthalic acid, a succinic acid or an o-sulphobenzoic acid.

The groups denoted by X (other than hydrogen) function as releasable groups in the cyan couplers and are split off in the process of chromogenic development and impart to the couplers the characteristics of a 2-equivalent coupler. Fugitive groups of this kind have been described, for example, in DE-A-34 29 257, EP-A-0 112 514, EP-A-0 118 752, EP-A-0 113 124, EP-A-0 161 626 and EP-A-0 105 991.

The group denoted by Q in Formula I or Formula III combines with the N atom and the two carbonyl groups to complete a preferably 5-membered dicarbonimide ring which may be substituted or may be condensed with another carbocyclic or heterocyclic ring and may contain, for example, an optionally substituted, optionally partially or completely hydrogenated condensed benzine ring. Examples of such cyclic dicarbonimide groups completed by Q are illustrated by the following formulae:

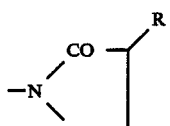 IVa

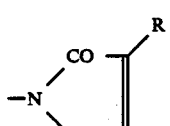 IVb (R = H, alkyl, alkenyl)

-continued

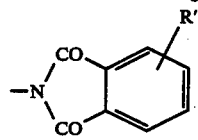

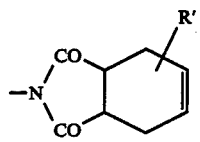

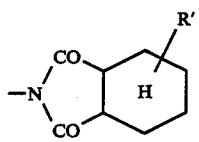

(R' = H or one or more identical or different groups such as halogen, alkyl, aryl, NO₂ or SO₃H).

The nature and size of the substituents denoted by R and R' are not critical for the process according to the invention since the dicarbonimide ring is a protective group for the 2-amino group and is removed in the course of the process so that the nature and size of the substituents R and R' are no longer evident in the end product of the process (Formula I). For convenience of preparation, however, it is advantageous to use a small protective group, if possible contributing not more than 50% to the total weight of the compound of Formula II. An alkyl group denoted by R, for example, should if possible have not more than 12 and preferably not more than 6 carbon atoms.

The process according to the invention is composed of the following steps 1 to 3:
1. Reduction of a 5-nitro compound corresponding to Formula II to the corresponding 5-amino compound. This may be achieved by the usual methods for reducing aromatic nitro compounds to the corresponding anilines. Hydrogenation with the aid of Raney-Nickel as hydrogenation catalyst, for example, is a suitable method.
2. Preparation of the 5-acylamino compound corresponding to Formula III from the corresponding 5-amino compound obtained in stage 1. Examples of suitable acylating agents include the corresponding acid chlorides of the formula R²—CO—Cl and the corresponding acid anhydrides but the 5-amino compounds may also be reacted with suitable isocyanates or carbamates to form the corresponding 5-ureido compounds. The following are examples of suitable isocyanates:

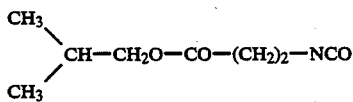

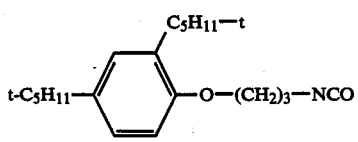

-continued

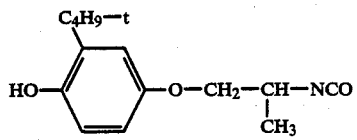

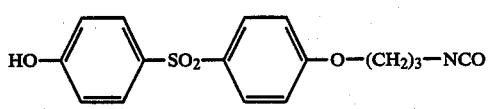

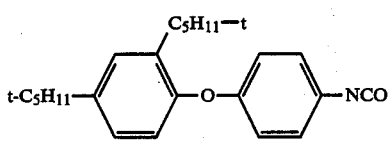

3. Preparation of the compounds corresponding to Formula I from compounds corresponding to Formula III by hydrolysis or hydrazinolysis. For suitable methods see Gibson and Bradshaw, Angew. Chem. 80, 986 (1986).

The combination of stages 1 to 3 provides an advantageous overall process for the preparation of compounds corresponding to Formula I. The required intermediate product corresponding to Formula II may easily be prepared by a reaction of the readily available 2-amino-5-nitrophenols with suitable dicarboxylic acid anhydrides, e.g. the anhydride of a substituted or unsubstituted succinic acid, maleic acid, phthalic acid, dihydrophthalic acid or hexahydrophthalic acid. Alternatively, the intermediate product corresponding to Formula II may be prepared by the reaction of a 2-halogen-5-nitrophenol with an alkali metal salt of a cyclic imide prepared from one of the above mentioned dicarboxylic acids, e.g. the potassium salt of succinimide or of phthalimide. The following are examples of suitable dicarboxylic acid anhydrides or imides:

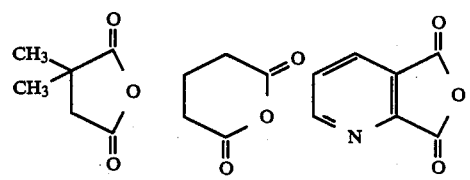

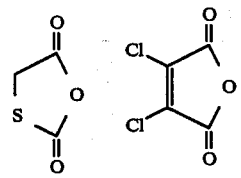

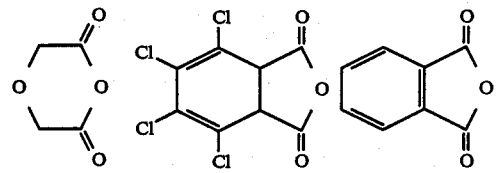

-continued

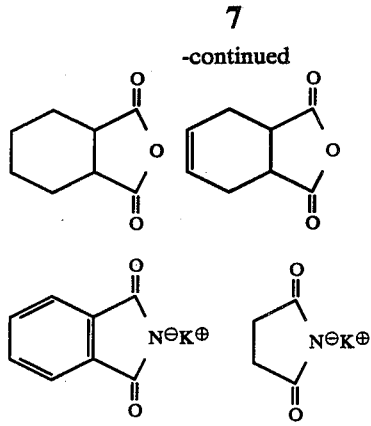

Compounds corresponding to Formula II

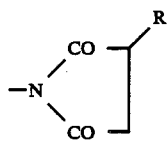

used as starting material for the process according to the invention wherein

X denotes H or Cl and

Q denotes the group required for completing a cyclic dicarbonimide group corresponding to one of the Formulae IVa to IVe

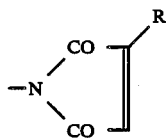  IVa

IVb (R=H or alkyl with up to 6 carbon atoms)

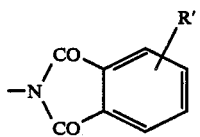  IVc

-continued

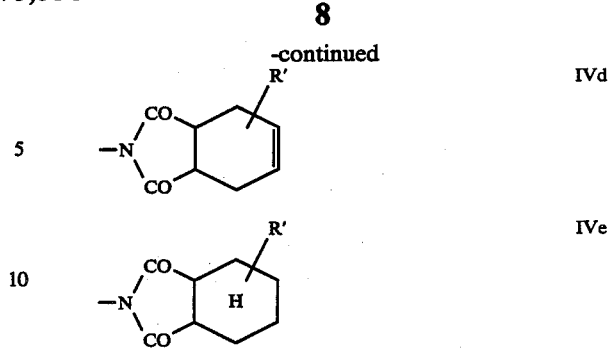  IVd

IVe (R'=H or alkyl with up to 6 carbon atoms) are new compounds.

In the intermediate product corresponding to Formula II, X primarily stands for hydrogen or halogen (e.g. chlorine), i.e. the intermediate products are generally prepared from a 2-halogen-5-nitrophenol or from 2-amino-5-nitro phenols in which the 4-position is unsubstituted or substituted with halogen. When cyan couplers having a releasable group (X) other than halogen are required, these may be obtained by the replacement of halogen by some other group in known manner at the stage of the intermediate product (II) but in many cases halogen or a releasable group different from halogen may be introduced at a later stage, e.g. in the finished cyan coupler. In that case, X in Formulae I, II and III denotes hydrogen.

The 5-acylamino-2-aminophenols of Formula I obtained by the process according to the invention may be converted by a single step into the desired cyan couplers, namely by also converting the 2-amino group into an acyl amino group.

The same acylating agents may be used for this reaction as those already mentioned in connection with the second stage of the process according to the invention, in particular acid halides of aliphatic or aromatic carboxylic acids, e.g. acid halides of substituted or unsubstituted aryl carboxylic acids (benzoic acid) or of aroxyalkyl carboxylic acids. The aryl or alkyl carboxylic acids may be partially or completely fluorinated. Cyan couplers containing a 2-arylureido group may be prepared by reaction of the 5-acylamino-2-aminophenols of Formula I with suitable isocyanates or carbamates in known manner.

The process according to the invention for the preparation of 5-acylamino-2-aminophenols and of the phenolic cyan couplers obtained therefrom has the following advantages:

1. Cost effective overall synthesis due to high volume/time yields;
2. Simple method of working up to the individual stages;
3. Different cyan couplers can be prepared by a single reaction stage from the previously prepared 5-acylamino-2-aminophenol.

Examples of cyan couplers prepared by the process according to the invention are shown below:

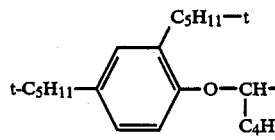  C-1

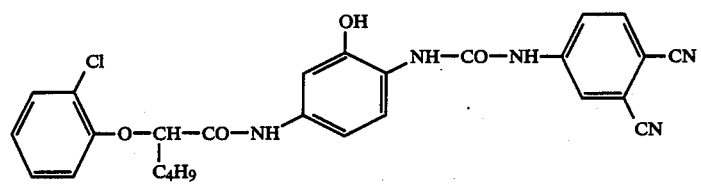
C-2
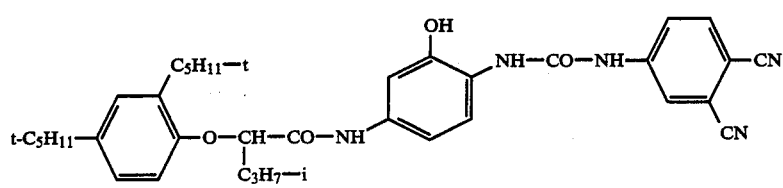
C-3
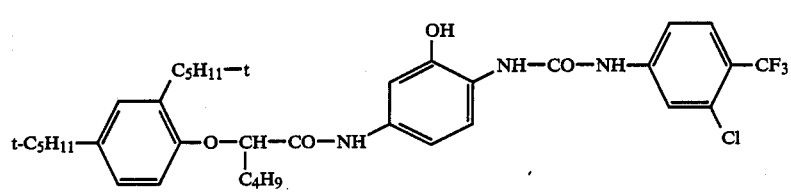
C-4
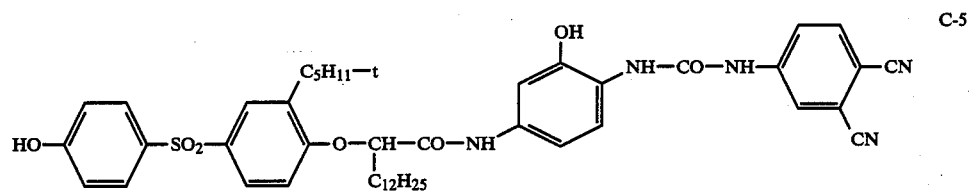
C-5
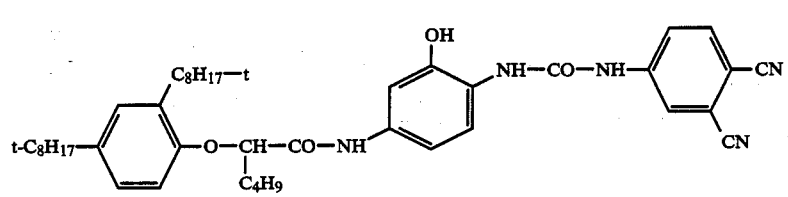
C-6
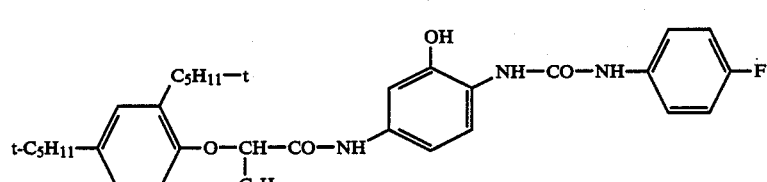
C-7
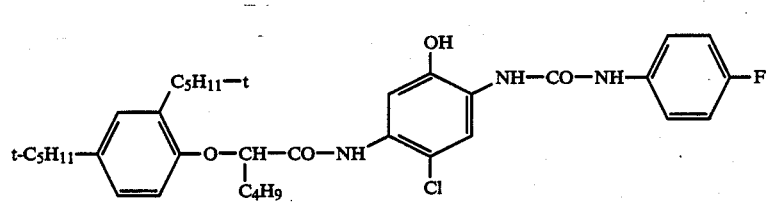
C-8
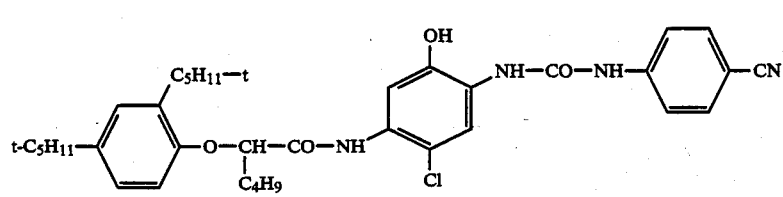
C-9

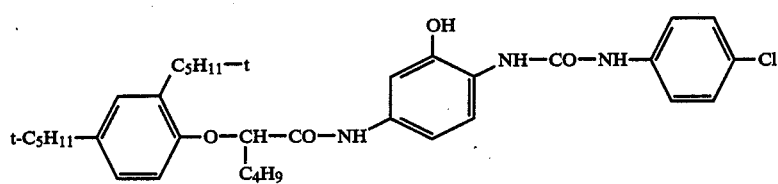
C-10
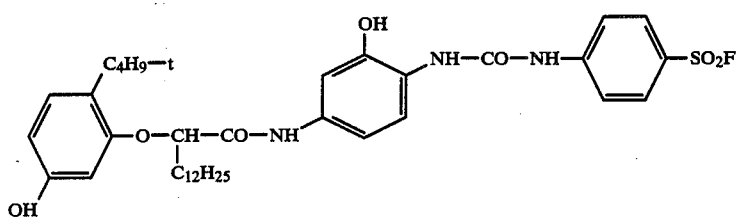
C-11
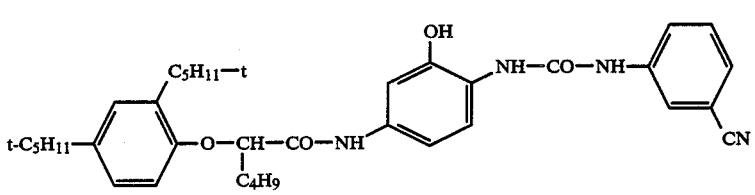
C-12
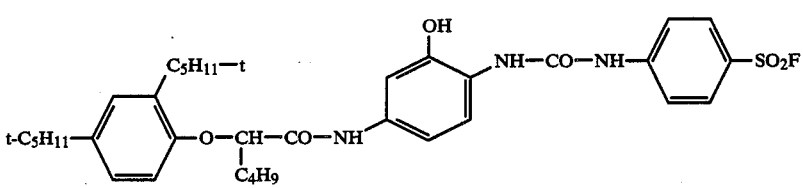
C-13
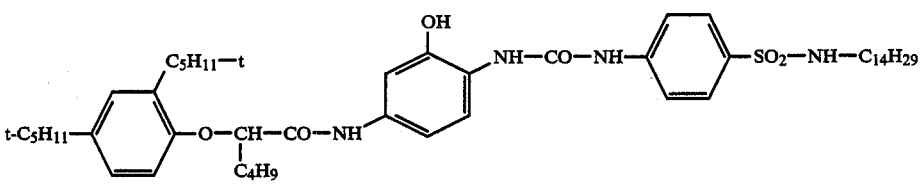
C-14
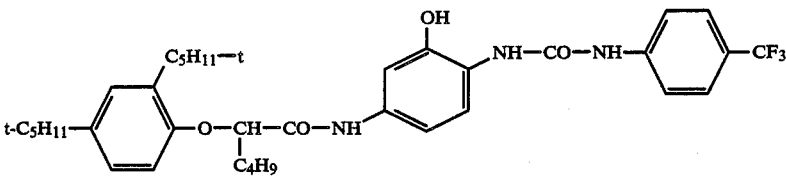
C-15
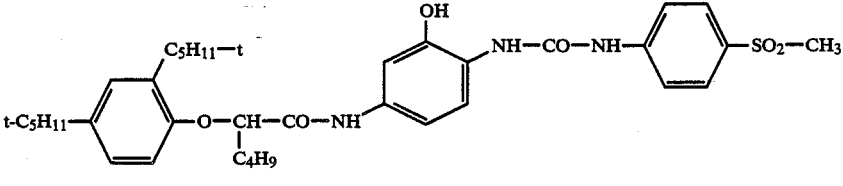
C-16
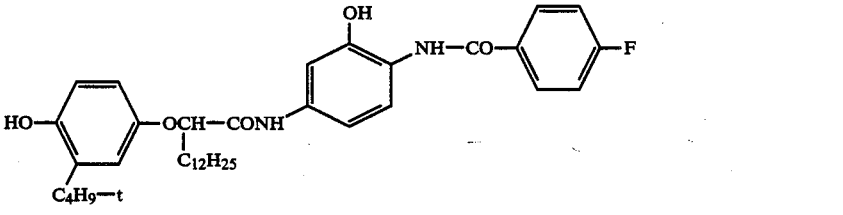
C-17

-continued
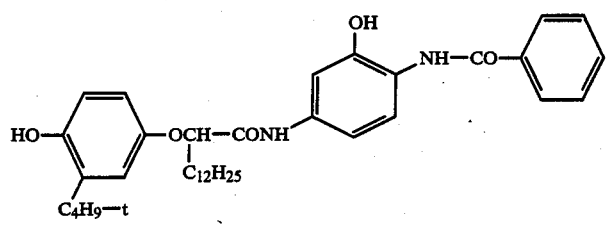
C-18
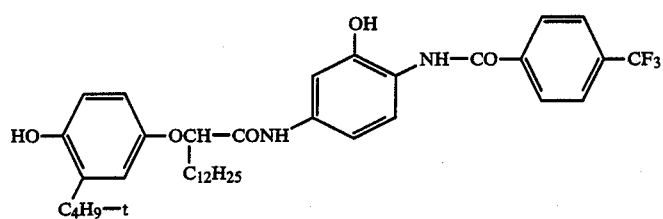
C-19
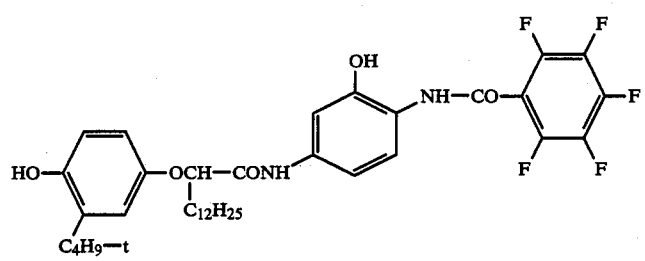
C-20
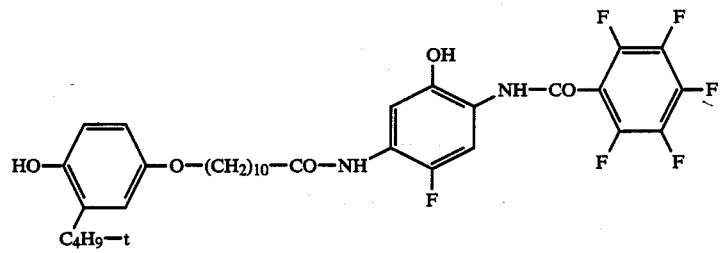
C-21
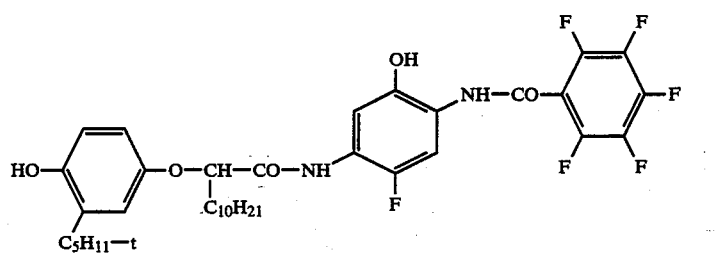
C-22
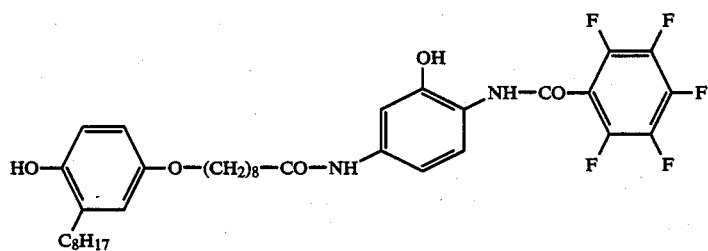
C-23

-continued
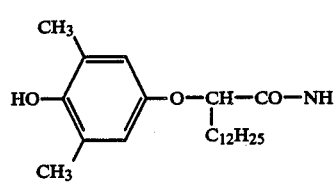 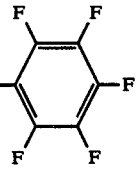
C-24
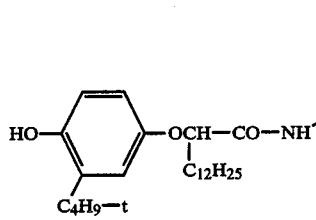
C-25
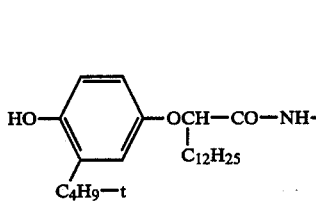
C-26
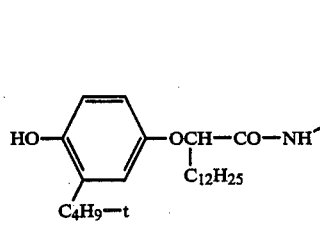
C-27
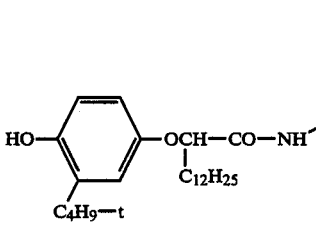
C-28
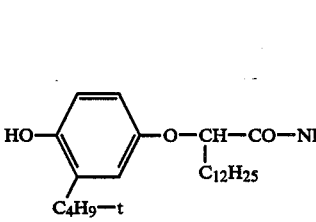
C-29
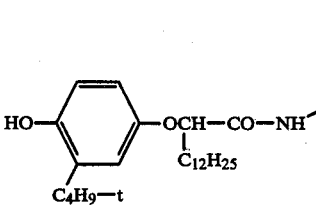
C-30

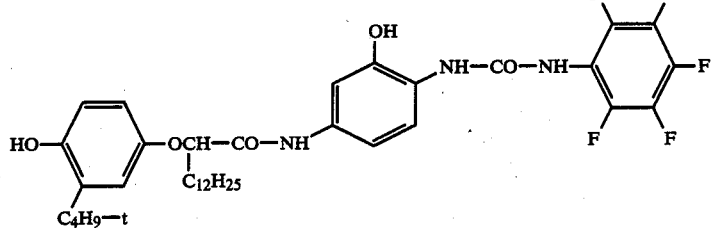

C-31

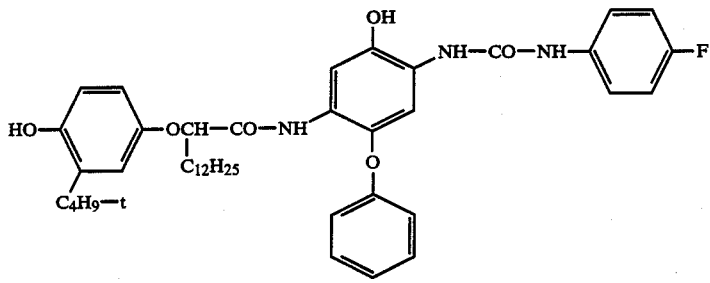

C-32

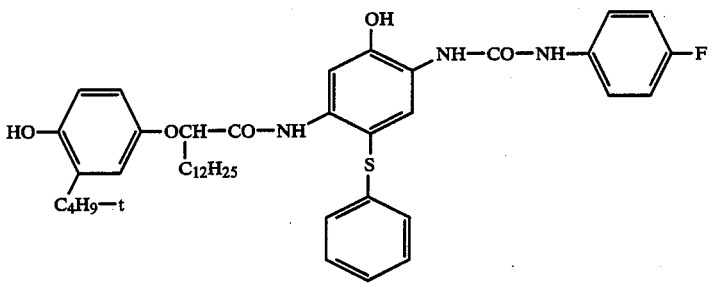

C-33

EXAMPLE 1

(Intermediate product)

N-(4-nitro-2-hydroxyphenyl)-phthalimide (Formula II)

231 g (1.5 mol) of 5-nitro-2-aminophenol and 444 g (3 mol) of phthalic acid anhydride were stirred together in 2.25 liters of acetic acid at boiling point for 2.5 hours. The product was suction filtered at room temperature, washed with water and dried. Yield: 420 g=98.5%.

EXAMPLE 2

(First stage)

N-(4-amino-2-hydroxyphenyl)-phthalimide 40 g of Raney-Nickel (washed neutral) were added to 284 g (1 mol) of N-(4-nitro-2-hydroxyphenyl)-phthalimide in 1.75 liters of dimethyl formamide (DMF) and the phthalimide was hydrogenated under a pressure of 15-20 bar at 60° C. The filtrate was precipitated in 3.5 liters of water, suction filtered, washed and dried. Yield: 230 g=90% of theoretical yield.

EXAMPLE 3

(Second stage)

N-[4-(α-2,4-bis-t-pentylphenoxy-hexanoylamido)-2-hydroxyphenyl]-pthalimide 385 g (1.05 mol) of α-(2,4-bis-t-pentylphenoxy)-hexanoyl chloride were added to 254 g (1 mol) of N-(4-amino-2-hydroxyphenyl)-phthalimide and 126 g (1.5 mol) of sodium bicarbonate in 1 liter of acetonitrile. The product was suction filtered after 20 hours, washed with acetonitrile stirred up with water, neutralised with 2N hydrochloric acid and finally washed with methanol. Yield: 560 g=96% of theoretical yield.

EXAMPLE 4

(Third stage)

2-amino-5-[α-(2,4-bis-t-pentylphenoxy)-hexanoylamino]-phenol (Formula I)

584 g (1 mol) of N-[4-(α-2,4-bis-t-pentylphenoxy-hexanoyl amido)-2-hydroxyphenyl]-phthalimide and 50 g (1 mol) of hydrazine hydrate were stirred together in 1 liter of acetonitrile at boiling point for 30 minutes. After cooling, the filtrate was stirred into 5 liters of H₂O/methanol (4:1). The precipitate obtained was suction filtered, washed and dried. Yield: 440 g=97% of theoretical yield.

EXAMPLE 5

Coupler C-1

454 g (1 mol) of 2-amino-5-[α-(2,4-bis-t-pentylphenoxy)-hexanoylamino]-phenol, 268.25 g (1.02 mol) of phenyl(3,4-dicyanophenyl)-carbamate and 14 ml of triethylamine were stirred together in 3.5 liters of acetonitrile at boiling point for 30 minutes. The reaction mixture was then cooled and the triethylamine was neutralised with acetic acid. The product was recrystallized from acetonitrile/ethyl acetate (9:1). Yield: 530 g=85% of theoretical yield.

We claim:

1. Process for the preparation of compounds corresponding to Formula I

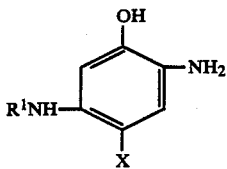

wherein
R[1] denotes an acyl group derived from an aliphatic or aromatic carboxylic or sulfonic acid or from a carbamic or sulfamic acid and X denotes hydrogen, halogen, alkoxy, aroxy, SO$_3$H or a heterocyclic group attached through —O— or —N<, characterised in that a compound corresponding to Formula II

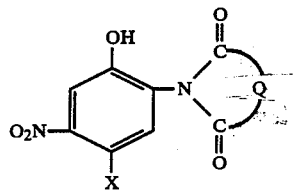

wherein
X has the meaning indicated and
Q denotes the group required for completing a dicarbonimide ring is converted by reduction to the amino compound and acylation into a compound corresponding to Formula III

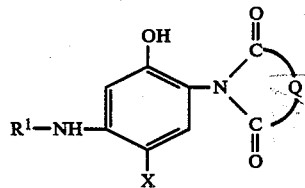

wherein
X, Q and R[1] have the meanings indicated, and in that the compound corresponding to Formula III is converted into the corresponding compound of Formula I by hydrazinolytic decomposition of the dicarbonimide ring.

2. Process as claimed in claim 1, wherein Q in Formulae II and III denotes a group for completing a succinimide ring of Formula IVa or maleic imide ring of Formula IVb

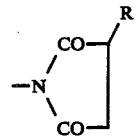

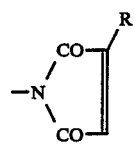

wherein
R represents H, alkyl or alkenyl; or a succinimide or maleic imide ring having condensed thereto a 6-membered carbocyclic ring.

3. Process as claimed in claim 1, wherein the amine obtained from the compound of Formula II by reduction is reacted with an acid chloride of the Formula R$^2$—CO—Cl wherein R$^2$ denotes an aryl group, an alkyl group with 1 to 20 carbon atoms or a substituted alkyl group corresponding to the following formula:

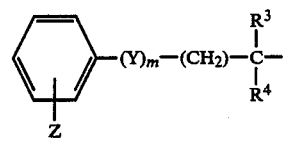

wherein
R$^3$ and R$^4$ represent, independently of one another, H or alkyl;
Y represents —O— or —S—;
Z represents one or more substituents selected from halogen, alkyl, alkoxy, alkylthio, alkylsulfonyl, carbonamido, sulfonamido and sulfamoyl;
m represents 0 or 1 and
n represents 0 or an integer from 1 to 3.

* * * * *